United States Patent [19]

Milich et al.

[11] Patent Number: 5,726,011
[45] Date of Patent: Mar. 10, 1998

[54] METHOD FOR DIAGNOSING CHRONIC HEPATITIS B VIRUS INFECTION

[75] Inventors: David R. Milich, El Cahon, Calif.; Toshiyuki Maruyama, Tokyo, Japan; Florian Schodel, Silver Springs, Md.; Darrel Peterson, Chesterfield, Va.

[73] Assignees: Virginia Commonwealth University, Richmond, Va.; The Scripps Research Institute, La Jolla, Calif.; Max Planck Gesellschaft, Munich, Germany

[21] Appl. No.: 221,098

[22] Filed: Mar. 31, 1994

[51] Int. Cl.⁶ .................................. C12Q 1/70
[52] U.S. Cl. .................. 435/5; 436/513; 436/820
[58] Field of Search .................. 435/5; 436/513, 436/820

[56] References Cited

U.S. PATENT DOCUMENTS 4,271,145  6/1981  Wands et al. .................. 435/70.21
4,547,368  10/1985  Tabor et al. .................. 424/227.1
4,710,463  12/1987  Murray .................. 435/69.3

FOREIGN PATENT DOCUMENTS 87117370  11/1987  European Pat. Off.

OTHER PUBLICATIONS

Stannard et al., "Antigenic Cross-reactions between Woodchuck Hepatitis Virus and Human Hepatitis B Virus Shown by Immune Electron Microscopy." J. Gen. Virol. 64:957–980, 1983.

*Primary Examiner*—Mary E. Mosher
*Assistant Examiner*—Donna C. Wortman
*Attorney, Agent, or Firm*—Fish & Richardson, P.C.

[57] ABSTRACT

Human antibodies that bind to woodchuck hepatitis virus core antigen are elevated in chronic hepatitis B patients in comparison to acute hepatitis B patients. Immunoassays for detection of the level of anti-WHV core antigen antibodies is used to distinguish chronic from acute hepatitis B patients.

11 Claims, 8 Drawing Sheets

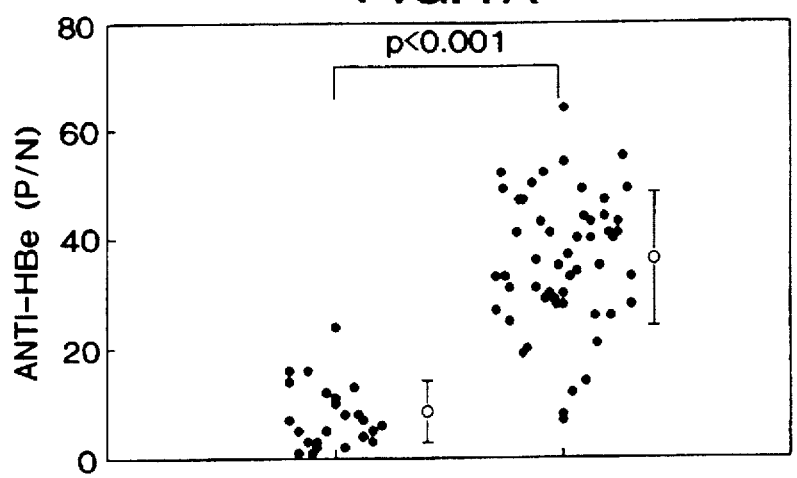
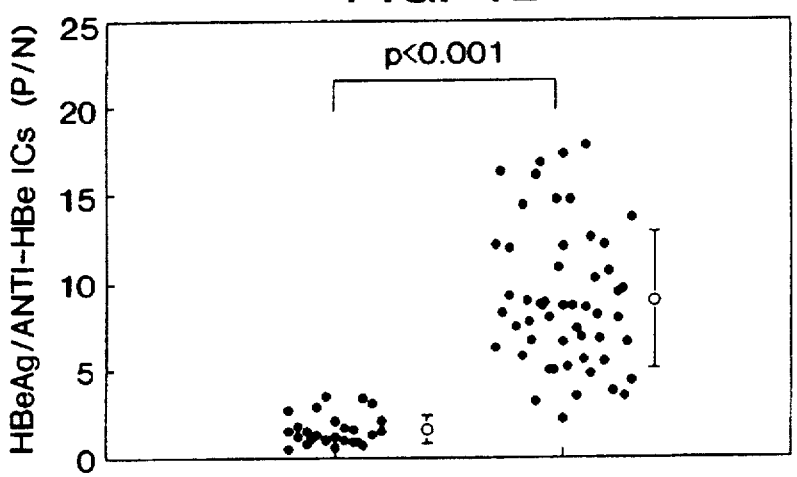
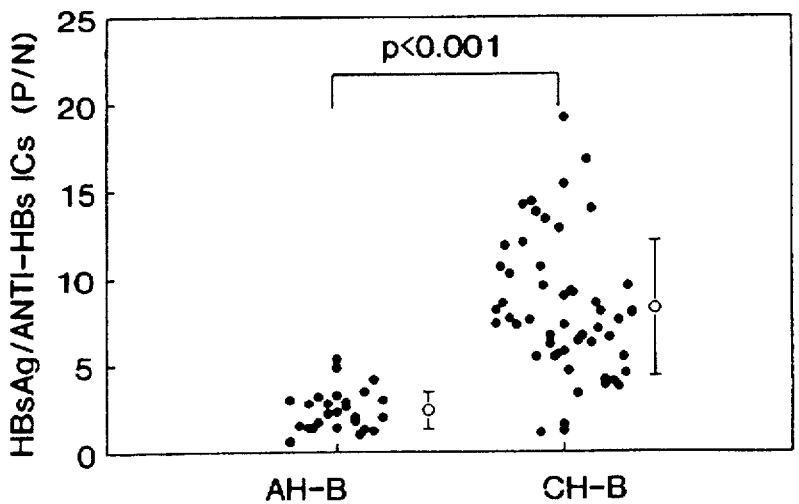

Anti-HBc$^w$

Anti-HBc

METHOD FOR DIAGNOSING CHRONIC HEPATITIS B VIRUS INFECTION

This invention was made with Government support under Grant No. AI-20720 awarded by the National Institute of Health. The Government has certain rights in this invention.

BACKGROUND OF THE INVENTION

1. Field of the Invention

The present invention relates generally to the hepatitis B virus (HBV) and specifically to a method for diagnosing chronic hepatitis B virus infection.

2. Description of Related Art

Infection with hepatitis B virus (HBV) is a worldwide public health problem, with chronic carriers accounting for approximately 10 percent of the population of Asia and Africa. Major causes of HBV-associated mortality include chronic active hepatitis, liver cirrhosis and hepatocellular carcinoma. Both chronic carriers and newly infected individuals are at risk of succumbing to such complications. One important transmission route is the infection of newborn infants at parturition by mothers who have active infections or are chronic carriers. Other routes for transmission include contaminated blood or blood products used to treat other health problems.

Infection with HBV often results in subclinical or acute self-limited liver disease or can result in chronic long-term infection. Chronic HBV infection elicits a spectrum of disease entities ranging from the most severe form of chronic active hepatits (CAH) to less severe chronic persistent hepatitis (CPH) to the asymptomatic carrier (ASC) state. An array of diagnostic assays have recently been developed to aid the clinician in differentiating hepatitis B virus infections from other forms of viral hepatitis (i.e., HAV, HEV, HCV). However, the ability to distinguish between an acute hepatitis B (AH-B) infection and symptomatic chronic hepatitis B (CH-B) infection is still problematic. This is especially true since CAH and CPH patients often demonstrate a cyclic pattern of hepatitis characterized by acute exacerbations (A.E.) of liver injury alternating with normal liver function.

After infection with HBV, large quantities of the virus and associated particles are present in the serum. During the symptomatic phases of infection, both acute and chronic HBV patients have elevated liver enzyme levels, possess the hepatitis B surface antigen (HBsAg) in their serum, and produce antibodies to the nucleocapsid antigen (HBcAg). Antibodies specific for the HBsAg or the hepatitis B e antigen (HBeAg) are not detected. The appearance of antibody to HBsAg is usually not observed until approximately two months following disappearance of circulating HBsAg. The viral particles present in the serum are known to shed their surface coat exposing the nucleocapsid, known as the core antigen (HBcAg). Antibody production to HBcAg occurs early in the course of the acute phase of HBV infection and can persist for many years, and chronically infected patients produce high titers of anti-HBc antibodies.

Previous studies have indicated that the nucleocapsids of the HBV and the woodchuck hepatitis virus (WHV) share a crossreactive epitope (Werner, et al., *J. Virol.* 1:314, 1979; Millman, et al., *Infection and Immunity* 2:752, 1982; Stannard, et al., *J. Gen. Virol.* 64:975, 1983; Ponzetto, et al., *Virus Research* 2:301, 1985). Prior to the present invention, it was not known whether human anti-HBc antibodies recognized woodchuck hepatitis nucleocapsid antigen (WHcAg) or if sera from patients at different stages of HBV infection could be distinguished based on differential reactivity to WHcAg. In contrast to most viral infections, acute and chronic HBV infected patients often produce both IgM and IgG anti-HBc antibodies, therefore, the mere presence of IgM anti-HBc is not diagnostic of an acute infection. However, higher levels of IgM anti-HBc are generally produced during the acute phase as compared to chronic infection, and this quantitative difference has become the only serologic means of differentiating an acute HBV infection from an A.E. of a chronic infection. The usefulness of IgM anti-HBc assays in the differentiation of acute from chronic HBV infection has also been questioned. The distinction between acute and chronic HBV infection is important in terms of prognosis and possible treatment modalities.

Thus, there exists a need for a simple, inexpensive and reliable assay to distinguish patients with acute HBV infection from those with chronic HBV infection. The present invention provides such an assay.

SUMMARY OF THE INVENTION

The present invention is based on the unexpected discovery that subjects with acute and chronic hepatitis B virus infection can be easily distinguished based on the level of antibody to HBcAg$^w$.

In one embodiment the invention provides an assay for diagnosing chronic HBV infection in a subject by detecting IgG anti-woodchuck hepatitis core antigen antibody in a subject.

In another embodiment, the above-described assay is performed in conjunction with detection of IgM HBcAg antibodies and the ratio of IgM HBcAg:IgG HBcAg$^w$ antibodies is determined.

In yet another embodiment, the invention provides a series of assays which include detection of serum levels of anti-HBe antibody, HBeAg/anti-HBe immune complex (IC) and HBsAg/anti-HBs ICs, all of which are significantly elevated in chronic versus acute hepatitis B patients.

BRIEF DESCRIPTION OF THE DRAWINGS

FIG. 1 is a comparison between acute hepatitis B (AH-B) and chronic hepatitis B (CH-B) patient serum levels of anti-HBe (panel A), HBeAg/anti-HBe ICs (panel B) and HBsAg/anti-HBs ICs (panel C).

DETAILED DESCRIPTION OF THE INVENTION

Figure 2A:
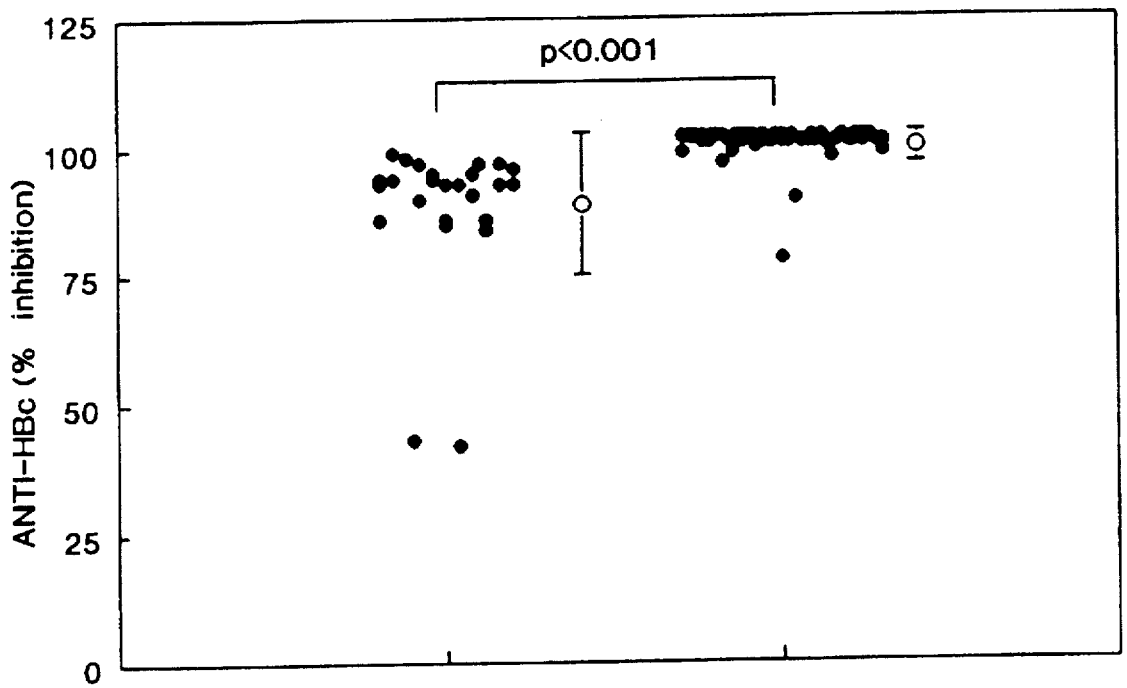
FIG. 2 is a comparison between acute hepatitis B (AH-B) and chronic hepatitis B (CH-B) patient serum levels of anti-HBc, IgM anti-HBc, IgG anti-HBc$^w$, and IgM anti-HBc/IgG anti-HBc$^w$ ratio. (Panel A=total anti-HBc; Panel B=IgM anti-HBc; Panel C=IgG anti-HBc$^w$; and Panel D=ratio of IgM anti-HBc/IgG anti HBC$^w$.)
Figure 2B:
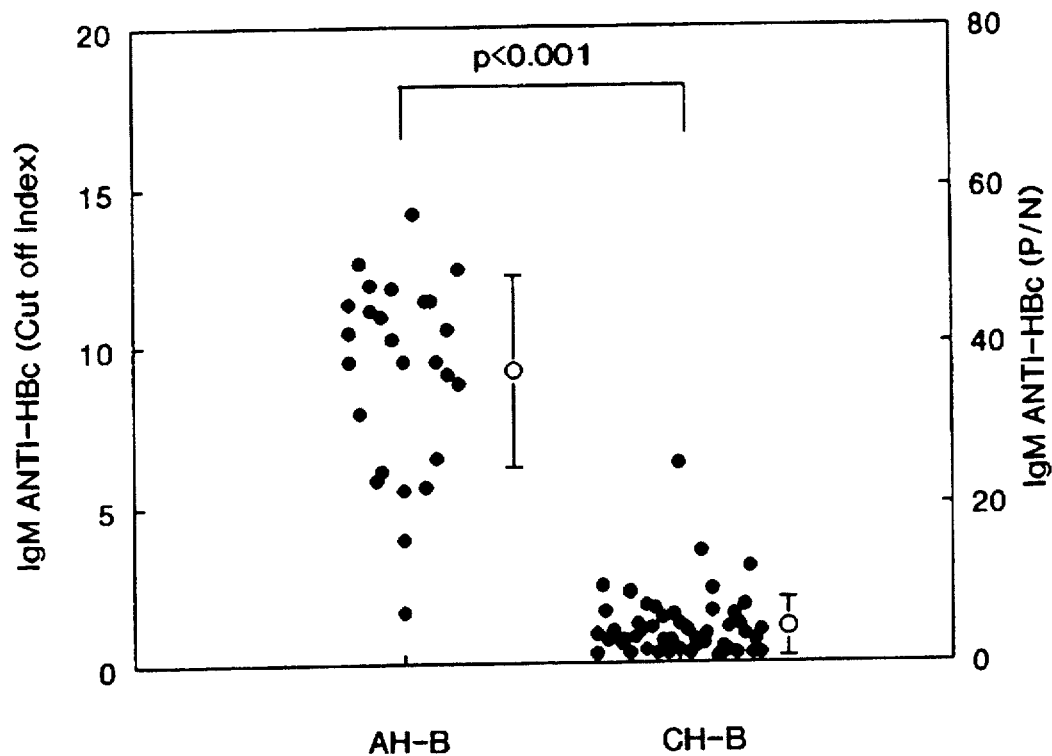
Figure 2C:
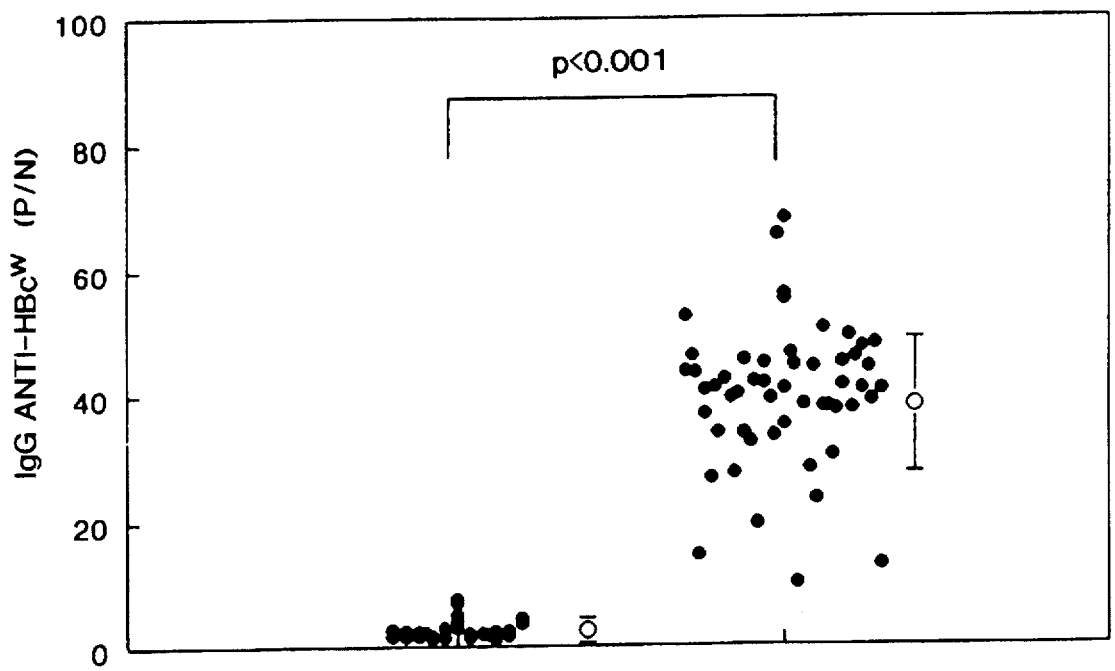
Figure 2D:
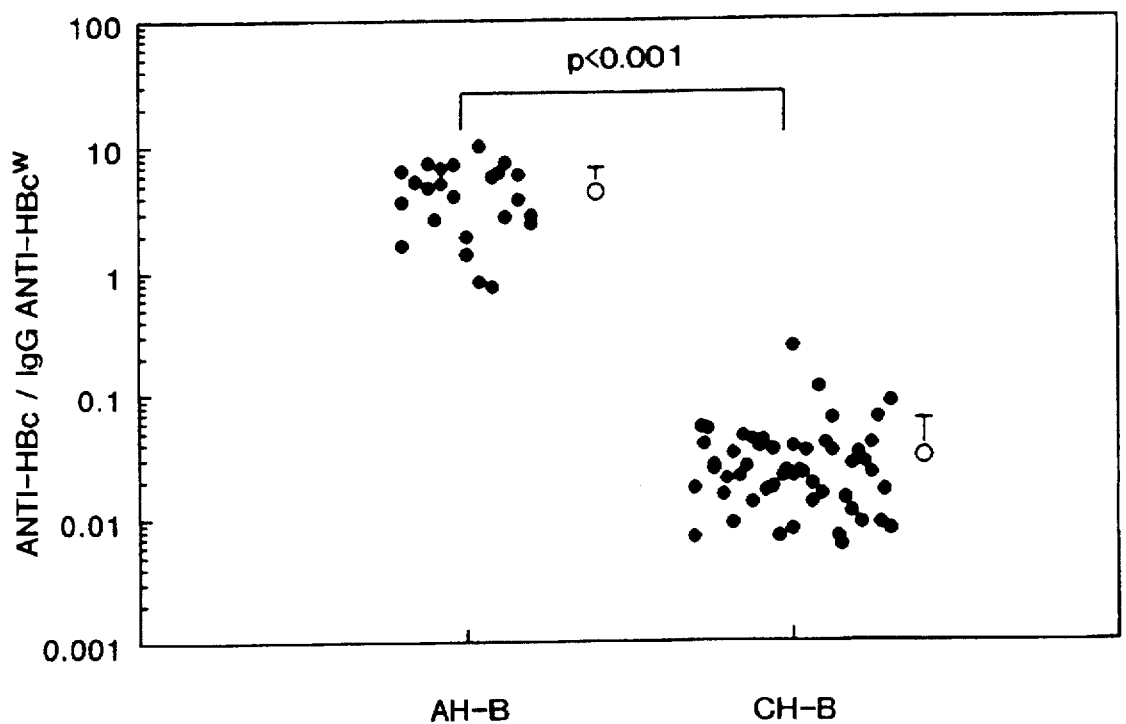

The present invention provides a sensitive new assay which detects antibody to woodchuck hepatitis core antigen (WHcAg) and distinguishes chronic from acute hepatitis B infection. The assay is based on the unexpected finding that patients with chronic hepatitis B infection have elevated serum levels of a species of anti-HBc antibody that cross-reacts with woodchuck hepatitis core antigen (i.e., anti-HBc"). In another embodiment, the invention provides a series of assays which include detection of serum levels of anti-HBe antibody, HBeAg/anti-HBe immune complexes (IC) and HBsAg/anti-HBs ICs, all of which are shown in the present invention to be significantly elevated in chronic versus acute hepatitis B patients.

The invention provides a method for diagnosing chronic hepatitis B virus (HBV) infection in a subject comprising contacting a sample from a subject suspected of having chronic HBV with an epitope that contains the amino acid sequence of a woodchuck hepatitis virus antigen wherein the epitope binds with antibody to woodchuck hepatitis B core antigen and detecting the presence of antibody that reacts with woodchuck hepatitis B core antigen in the sample. The subject can be any animal and preferably is a human.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The method of the invention for detection of anti-woodchuck hepatitis B core antigen antibodies (anti-HBc") in a sample is performed in vitro, for example, in immunoassays in which the antibodies can be identified in liquid phase or bound to an antigen or epitope that is bound to a solid phase carrier. In addition, an antibody for detection of anti-woodchuck HBc antibodies in these immunoassays can be detectably labeled in various ways. Examples of types of immunoassays which can be utilized to detect anti-woodchuck HBc antibodies in a sample, include competitive and non-competitive immunoassays in either a direct or indirect format. Examples of such immunoassays are the radioimmunoassay (RIA) and the sandwich (immunometric) assay. Detection of the antibodies using the method of the invention can be done utilizing immunoassays which are run in either the forward, reverse, or simultaneous modes, including competition immunoassays and immunohistochemical assays on physiological samples. Those of skill in the art will know, or can readily discern, other immunoassay formats without undue experimentation.

The woodchuck HBc antigen (WHcAg), or epitopes thereof, can be bound to many different carriers and used to detect anti-woodchuck HBc antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antigen or epitopes, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the antibodies used in the method of the invention can be done using standard techniques common to those of ordinary skill in the art.

For purposes of the invention, antibodies that bind to woodchuck HBcAg may be detected using anti-human IgG antibodies. Any sample containing a detectable amount of woodchuck HBcAg antibody can be used. A sample can be a liquid such as urine, saliva, cerebrospinal fluid, blood, serum and the like. Preferably, the sample is serum.

The invention also provides a series of assays which include detection of serum levels of anti-HBe antibody, HBeAg/anti-HBe immune complexes (IC) and HBsAg/anti-HBs ICs, all of which are significantly elevated in chronic versus acute hepatitis B patients. The detection of these antigens and antibodies is performed according to methods described above for the detection of anti-woodchuck hepatitis virus antibodies. For example, to detect, anti-HBe antibody, HBe antigen or peptide containing an epitope can be fixed to a solid support and a species specific antibody which binds to the anti-HBe antibody added after the antigen and antibody in the sample react. Similarly, the immune complexes can be detected in a sample by reaction with a second antibody that binds to the antigen in the complex and a third antibody which binds to the antibody in the complex. For example, a non-competitive monoclonal antibody specific for HBsAg or HBeAg is fixed to a solid support and a serum sample is added followed by the addition of a labeled monoclonal antibody to human IgG.

The P/N ratio, which represents the level of antibody and ICs in the sample (P) as compared to the level of antibody and ICs in control sera, is preferably greater than about 2 as a lower limit or cut-off, and most preferably greater than 3. Preferably, the detection is performed by determining the absorbance ($OD_{492}$) value of the sample and the control sera. Those of ordinary skill in the art will know of other techniques for determining the level of antibody or IC's in a sample.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a woodchuck HBcAg or woodchuck HBcAg epitope, and another container may comprise an anti-human antibody which is, or can be, detectably labelled.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich immunoassays.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

In performing the assays, it may be desirable to include certain "blockers" in the incubation medium (usually added with the labeled soluble antibody). The "blockers" are added to assure that non-specific proteins, proteases, or antiheterophillic immunoglobulins to anti-HBc$^w$ immunoglobulins, for example, present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific antibodies of the same class or subclass (isotype) as those used in the assays (e.g., IgG1, IgG2a, IgM, etc.) can be used as "blockers". The concentration of the "blockers" (normally 1–100 µg/µl) is important, in order to maintain the proper sensitivity yet inhibit unwanted interference by mutually occurring cross reactive proteins in the specimen.

The assays of the invention include using antibodies immunoreactive with WHcAg, HBcAg$^w$, HBcAg, HBeAg/anti-HBe ICs and HBsAg/anti-ABsAg ICs or fragments thereof. Monoclonal antibodies, such as those used in the present Examples, can be made by immunizing an appropriate host, such as a mouse, with antigen containing fragments of the whole protein by methods well known to those skilled in the art (Kohler, et al., *Nature*, 256:495, 1975). Antibodies with reactivity to ICs described herein are available commercially or can be produced as described in Maruyama, et al., (*J. Immunol Meth.*, 155:65, 1992). The term antibody, as used in this invention, is meant to include intact molecules as well as fragments thereof, such as Fab and F(ab')$_2$, which are capable of binding an epitopic determinant on the different HBV or WHV antigens.

The following examples are intended to illustrate but not limit the invention. While they are typical of those that might be used, other procedures known to those skilled in the art may alternatively be adopted without resort to undue experimentation.

EXAMPLE 1

MATERIALS AND METHODS

1. Recombinant Antigens and Synthetic Peptides

Recombinant HBcAg of the ayw subtype, recombinant HBeAg of the ayw subtype, and recombinant WHcAg were derived from *E. coli* expression vectors as previously described (Schödel, et al., *Vaccines* 90, Cold Spring Harbor Laboratory, pp. 193–198, 1990; Schödel, et al, *J. Biol. Chem.*, 268:1332–1337, 1993; Schödel, et al., *Vaccine*, 6:624–628, 1993 (shows the nucleotide/amino acid sequence for WHcAg)). Synthetic peptides derived from the WHcAg sequence were synthesized by the Merrifield solid-phase method, and were subjected to HPLC on a C18 reverse phase column. All peptides used eluted as a single major peak (>90%). Synthetic peptides were produced in the peptide laboratory of the R. W. Johnson Pharmaceutical Research Institute by G. B. Thornton (La Jolla, Calif.).

2. Antibodies

Murine polyclonal anti-HBc, anti-WHc and rabbit polyclonal anti-WHc were produced by immunization with recombinant HBcAg or WHcAg. Polyclonal rabbit anti-HBc was purchased from DAKO (CA). Monoclonal (Mab) anti-HBc (3105, 3120), anti-HBe (904, 905) and anti-HBeAg peptide (2221) antibodies were provided by M. Mayumi (Jichi Medical College, Japan) (Takahashi, et al., *J. Immunol.*, 130:2903–2907, 1983; Imai, et al., *J. Immunol.*, 128:69–72, 1982; Takahashi, et al., *J. Immunol.*, 147:3156–3160, 1991). These antibodies can be purchased from the Institute of Immunology, Japan. Monoclonal anti-HBc (440, 442), and anti-HBe (420, 422, 426) antibodies were obtained from Green Cross (Osaka, Japan). Peroxidase conjugated Mab anti-human IgG was provided by Ortho Diagnostics (NJ). Peroxidase-conjugated polyclonal goat anti-mouse or rabbit Ig was purchased from Boehringer Mannheim (IN).

3. Direct Solid-Phase Enzyme Immunoassays

Solid-phase enzyme immunoassays (EIA) were used to measure serum anti-HBc$^w$, IgG anti-HBc, IgM anti-HBc or anti-HBe levels. Recombinant WHcAg, HBcAg or HBeAg were coated onto microtiter plates (50 ng/well) overnight at 4° C., the plates were preincubated for 1 hour at 37° C. with 50 µl of PBS containing 1% BSA, 0.005% Tween 20, and 5% heat inactivated goat serum (blocking buffer). Human sera were diluted 1/500 in blocking buffer and added to the plates and incubated for 2 hours. The plates were incubated with 50 µl of peroxidase conjugated anti-human IgG (1:3000) or anti-human IgM (1:1000) for 2 hours. The plates were developed by a final incubation for 10 min. with 50 µl of orthophenylene diamine (OPD). The absorbance was read on an automatic microtiter plate reader. The data are expressed as a P/N ratio, which represents the absorbance (OD$_{492}$) value of the sample (P) as compared to the mean absorbance value of at least 15 control sera.

Quantitation of serum IgM anti-HBc was also performed by using the Abbott Corzyme-M kit (Abbott Labs, Chicago, Ill.) according to the manufacturer's procedure. A cut-off value of 0.25 times the positive control mean (PC) plus the negative control mean (NC) was calculated (0.25×PC+NC), and the sample/cut-off ratio was defined as the cut-off index (C.I.) according to the manufacturer. At the same time, quantitation of serum IgM anti-HBc was performed using the direct EIA. There was a high correlation in IgM anti-HBc values in sera tested in the Corzyme-M kit versus the direct EIA (p<0.001, r=0.62, n=86). Detection of total serum anti-HBc was also performed by using the Abbott Corzyme kit (Abbott Labs, Chicago, Ill.) according to the manufacturers procedure. In this assay, anti-HBc was expressed as a percent inhibition, and inhibition of more than 50% is considered positive for anti-HBc.

4. Quantitative HBsAg or HBeAg-Specific Immune Complexes Assays

To detect HBsAg or HBeAg-specific immune complexes in human serum, a solid phase EIA has been developed (Maruyama, et al., *J. Immunol. Meth.*, 155:65–75, 1992). Briefly, plates were coated with monoclonal antibody (0.5 µg/ml) specific for either HBsAg (1B1E7F7) (Ortho Diagnostic, N.J.) or specific for HBe Ag-specific peptide (2221) as the capture reagents. These solid phase Mabs were chosen because they were previously demonstrated to bind immune-complexed as well as free antigen. Test sera diluted 1/25 in blocking buffer were added to the wells coated with solid-phase Mabs and the plates were washed after a 2 hr. incubation. The serum anti-HBs or anti-HBe antibody component of the IC was then detected with peroxidase-labeled monoclonal antibody to human IgG. The data are expressed as a P/N ratio, which represents the absorbance (OD$_{492}$) value of the sample (P) as compared to the mean absorbance value of at least 15 control sera.

5. Patients.

Twenty-six patients with acute hepatitis type B (AH-B), fifty-three patients with chronic hepatitis-B (CH-B) including twelve patients with chronic persistent hepatitis (CPH) and forty-one patients with chronic active hepatitis (CAH) were studied. The diagnosis of AH-B was based on the findings of elevated values of serum alanine aminotransferase (ALT) (at least 10 times the upper limit of normal), associated with the detection of HBsAg and IgM anti-HBc antibodies in the serum together with the recent onset of jaundice and other typical symptoms of acute hepatitis. All AH-B patients were known to be HBsAg negative prior to liver injury. Furthermore, all AH-B patients recovered completely from illness, with normalization of ALT and clearance of HBsAg from the serum. All CH-B patients in this study who were persistently positive for HBsAg and HBeAg in their serum for more than 1 year, were diagnosed as CPH or CAH by histology. All AH-B patients were followed at the First Department of Internal Medicine, Tokyo University (Tokyo, Japan). All sera were tested for HBsAg/anti-HBs, HBeAg/anti-HBe, anti-HBc, IgM anti-HBc, IgM anti-hepatitis A virus, anti-HDV and anti-HCV by using commercial enzyme immunoassays (EIAs; Abbott Laboratories) in addition to the experimental assays for IgM anti-HBc, IgG anti-HBc, anti-HBe, anti-HBc$^w$, and HBsAg or HBeAg-specific immune complexes measured by direct solid-phase EIAs. All AH-B and CH-B patients were negative for IgM-anti-HAV, anti-HDV and anti-HCV. As controls for the novel anti-HBc$^w$ assay, sera were collected from an additional 26 healthy controls, 7 acute hepatitis A, 8 acute hepatitis C, 30 chronic hepatitis C, and 10 HBsAg-positive and HBeAg-negative chronic hepatitis B patients.

HBV-DNA was determined using a dot blot procedure (Lieberman, et al., *Hepatology*, 3:285–291, 1983). Briefly, 10 µl of serum was denatured and applied to a nitrocellulose membrane under vacuum. Hybridization was performed using $^{32}$P labeled cloned HBV-DNA (specific activities; 2–4×10$^8$ cpm/µg). The membranes were autoradiographed for 96 hours on X-ray films. Serially diluted, known quantities of cloned HBV-DNA served as positive controls, and 0.5 pg of HBV-DNA was detectable in the assay.

Comparison between mean values in all assays was determined by Student's t-test. A p value <0.05 was considered significant.

EXAMPLE 2

COMPARISON OF THE PREVALENCE OF ANTI-HBe, HBeAg/ANTI-HBe ICs, AND HBsAg/ANTI-HBs ICs IN ACUTE AND CHRONIC HBV INFECTION

Serum samples from 26 acute hepatitis type B (AH-B) patients and 53 chronic hepatitis type B (CH-B) patients collected during period of peak alanine aminotransferase (ALT) elevations (mean ALT in AH-B patients 1790±1351 U/l; in CH-B patients 385±229 U/l) were analyzed for the presence of anti-HBe, HBeAg/anti-HBe immune complexes (ICs) and HBsAg/anti-HBs ICs by the experimental immunoassays described. Note that all AH-B and CH-B patient sera were negative for anti-HBe antibody when tested in a commercial assay (Abbott Laboratories). In contrast, when sera were analyzed by the direct EIA method all CH-B patients demonstrated significant anti-HBe antibody production (FIG. 1,A).

FIG. 1 shows a comparison between AH-B and CH-B patient serum levels of anti-HBe, HBeAg/anti-HBe ICs, and HBsAg/anti-HBs ICs. Serum samples from 26 AH-B and 53 CH-B patients were analyzed for (A) anti-HBe at a 1/500 dilution; (B) HBeAg/anti-HBe ICs at a 1/25 dilution; and (C) HBsAg/anti-HBs ICs at a 1/25 dilution in direct EIAs as described. Single serum samples were collected from each patient at the peak of ALT elevation representing the period of most severe liver injury. Results are expressed as a P/N (Positive/Negative) ratio and the mean ±s.d. for each patient group is also shown. N=0.016±0.0002 (anti-HBe assay); N=0.081±0.028 (HBeAg/anti-HBe ICs assay); and N=0.093±0.034 (HBsAg/anti-HBs ICs assay).

Although most AH-B patient sera were positive for anti-HBe, the sera of AH-B patients contained significantly less anti-HBe antibody as compared to CH-B patients. However, 13% of CH-B and 46% of AH-B patients exhibited overlapping levels of anti-HBe between 7.9 and 24.1 P/N values. This degree of overlap compromises the usefulness of this assay in terms of discriminating between AH-B and CH-B infection. Because the sera of AH-B and CH-B patients taken during periods of liver injury were also positive for the HBeAg, sera were analyzed for the presence of HBeAg/anti-HBe ICs (FIG. 1,B). The sera of CH-B patients contained significantly greater levels of HBeAg/anti-HBe ICs as compared to AH-B patient sera and the degree of overlap between the two patient groups was quite minimal (7% of CH-B and 19% of AH-B patients exhibited overlapping P/N values between 2.2 and 3.5). Similarly, CH-B patient sera contained significantly higher levels of HBsAg/anti-HBs ICs as compared to AH-B patient sera (FIG. 1,C). However, there was a significant overlap in the HBsAg/anti-HBs IC assay between P/N values of 1.1 and 5.4 amongst CH-B patients (18%) and AH-B patients (92%).

Cumulatively, the experimental assays for the measurement of anti-HBe, HBeAg/anti-HBe ICs, and HBsAg/anti-HBs ICs illustrate very significant differences in the mean levels of these parameters between AH-B and CH-B patient sera, however, complete discrimination based on any single assay would be difficult due to overlapping values at the margins (FIGS. 1A–C). However, all AH-B and CH-B patient sera were analyzed at the same single dilution (i.e., 1/500 for anti-HBe analysis; and 1/25 for IC analysis). It is possible that modifications in assay design may yield results more useful in discriminating between acute and chronic HBV patient groups.

EXAMPLE 3

COMPARATIVE LEVELS OF IgG ANTI-HBc, IgM ANTI-HBc AND ANTI-HBc$^w$ IN ACUTE AND CHRONIC HBV INFECTION

A commercial anti-HBc assay (Corzyme, Abbott Labs) modified by using 1/500 dilutions of sera was used to compare AH-B and CH-B patient sera for total anti-HBc. FIG. 2 shows a comparison between AH-B and CH-B patient serum levels of anti-HBc, IgM anti-HBc, IgG anti-HBc$^w$, and IgM anti-HBc/IgG anti-HBc$^w$ ratio. Serum samples from 26 AH-B and 53 CH-B patients were analyzed for (A) total anti-HBc at a dilution of 1/500 in the Corzyme assay (Abbott Laboratories); (B) IgM anti-HBc at a 1/1000 dilution in the Corzyme-M assay (Abbott Laboratories); (C) IgG anti-HBc$^w$ at a dilution of 1/500 in a direct EIA using WHcAg as the solid-phase ligand; and (D) the ratio of IgM anti-HBc/IgG anti-HBc$^w$. Single serum samples were collected from each patient at the peak of ALT elevation. Results are expressed as % inhibition in the anti-HBc assay, as a Cut-Off Index (C.I.) and as a P/N ratio in the IgM anti-HBc assay, and as a P/N ratio in the IgG anti-anti-HBc$^w$ assay. The mean ±s.d. for each patient group is also shown. N=4.6±9.5% (IgG anti-HBc assay); N=0.075±0.012 and 1 C.I. was 0.298 (IgM anti-HBc assay)l and N=0.014±0.002 (IgG anti-HBc$^w$ assay).

As previously shown, both AH-B and CH-B patients produce anti-HBc efficiently although CH-B patient sera demonstrated higher levels (101±3% inhibition) as compared to AH-B patient sera (89±15% inhibition) (p <0.001 ). A direct EIA was also used to measure IgG anti-HBc in AH-B and CH-B patient sera and the results were similar to the commercial assay. Even using 1/500 serum dilutions in both anti-HBc assays there was very significant overlap between AH-B and CH-B patients in terms of IgG anti-HBc values (FIG. 2, panel A). In contrast, use of the Corzyme-M kit (Abbott Laboratories) to measure IgM anti-HBc antibody illustrates the preferential production of IgM anti-HBc antibodies in AH-B patients as compared to CH-B patients (FIG. 2, panel B). The mean IgM anti-HBc level expressed as a Cutoff Index (C.I.) was 9.2±3.0 (or 37.0±12.1 P/N ratio) in AH-B patient sera and 1.1±0.9 C.I. (or 4.6±4.0 P/N ratio) in CH-B patients (p <0.001 ). Nonetheless, 20% of CH-B and 23% of AH-B patients exhibited IgM anti-HBc levels that overlapped between the 1.6 C.I. (6.6 P/N) and 6.3 C.I. (25.4 P/N) values.

Previous studies have indicated that the nucleocapsids of the HBV and the WHV share a crossreactive epitope(s) (Werner, et al., *J. Virol.*, 1:314–322, 1979; Millman, et al., *Infection and Immunity*, 2:752–757, 1982; Stannard, et al., *J. Gen. Virol*, 64:975–980, 1983; Ponzetto, et al., *Virus Research*, 2:301–315, 1985). Therefore, it was of interest to determine if human anti-HBc antibodies recognized WHcAg, and if AH-B and CH-B patient sera could be distinguished based on differential reactivity to WHcAg. For this purpose, a direct EIA was developed using recombinant WHcAg as solid-phase ligand and a monoclonal antibody (Mab) specific for human IgG as the probe.

Figure 3:
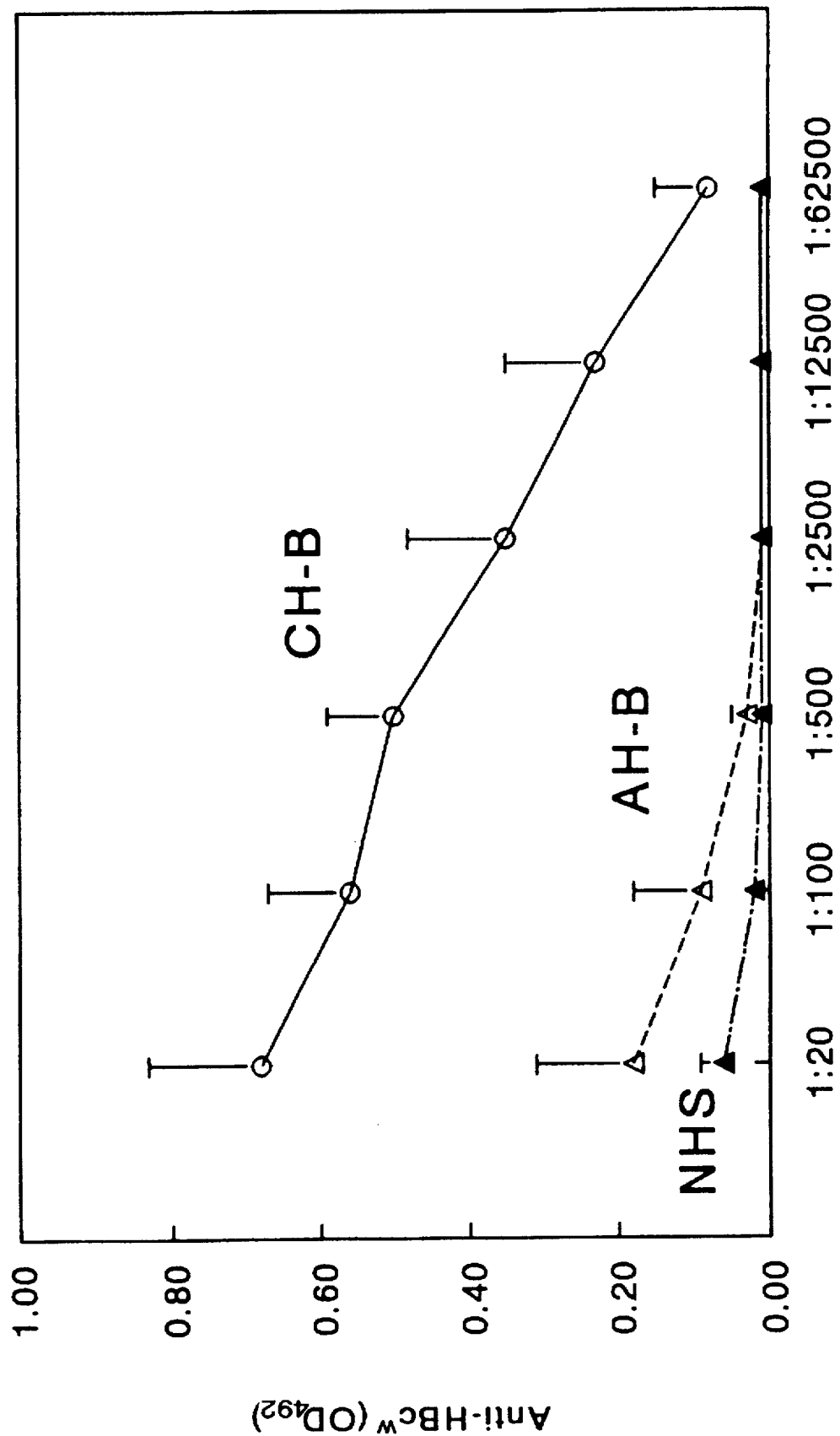
FIG. 3 is an endpoint titration of anti-HBc$^w$ IgG in AH-B (Δ-Δ) and CH-B (○-○) patient sera (▲-▲=normal human serum (NHS)).

FIG. 3 illustrates the end-point titrations of pools of 5 AH-B patient sera, 5 CH-B patient sera and 5 normal human sera (NHS) assayed for IgG binding to solid-phase WHcAg. The data are expressed as mean ±s.d. absorbance values ($OD_{492}$). The end-point titer of the CH-B patient sera was 1/62,500 as compared to 1/100 in AH-B patient sera. This result suggested that at least a proportion of human anti-HBc antibodies can crossreact on WHcAg, and that chronically infected HBV patients may preferentially produce this crossreactive specificity designated as anti-HBc$^w$.

Based on the end-point titration analysis, a 1/500 serum dilution was chosen to screen the 26 AH-B and 53 CH-B patient sera for IgG binding to solid-phase WHcAg (FIG. 2, panel C). The CH-B patient sera exhibited significantly higher levels of IgG anti-HBc$^w$ (P/N 37.5±10.5) as compared to AH-B patient sera (P/N 2.5±1.4) (p<0.001). Furthermore, there was no overlap between the IgG anti-HBc$^w$ values of AH-B and CH-B patient sera (FIG. 2, panel C). IgM anti-HBc$^w$ antibody production was also examined and no significant difference was observed between the low levels of IgM anti-HBc$^w$ produced in AH-B patients (P/N 2.1±1.6) and CH-B patients (P/N 2.4±4.2).

The IgM anti-HBc assay and the IgG anti-HBc$^w$ assays performed singly were the two most useful assays to discriminate between acute and symptomatic chronic HBV infection. However, performing both of these assays and expressing the results as a ratio of IgM anti-HBc/IgG anti-HBc$^w$ provided a very powerful serologic method of discriminating between AH-B and symptomatic CH-B infections.

EXAMPLE 4

PRODUCTION OF ANTI-HBc$^w$ IS UNIQUE TO HBV INFECTIONS

Before proposing the utilization of the anti-HBc$^w$ assay to distinguish between acute and chronic HBV infections, it was necessary to establish that anti-HBc$^w$ antibody production is specific to HBV infection and not a non-specific result of acute or chronic liver injury. In addition to the 53 HBeAg-positive CH-B patient sera previously described, 10 HBeAg-negative CH-B patient sera, 7 acute hepatitis A patient sera, 10 acute hepatitis C patient sera, 30 chronic hepatitis C patient sera, and 26 normal control sera were evaluated in the anti-HBc$^w$ assay (Table 1 ). Only HBsAg-positive, CH-B patients positive or negative for the HBeAg produced anti-HBc$^w$ antibody, and these patient groups produced anti-HBc$^w$ at a frequency of 100%.

TABLE 1

PRODUCTION OF ANTI-HBc$^w$ IgG IS UNIQUE TO HBV INFECTION

| Patients | No. | Mean ± s.d. | Range | Anti-HB$^w$ Frequency (%) |
|---|---|---|---|---|
| HBsAg (+) | | | | |
| HBeAg (+) CH-B | 53 | 0.556 ± 0.156 | 0.141–0.957 | 100 |
| HBeAg (−) CH-B | 10 | 0.494 ± 0.266 | 0.131–1.003 | 100 |
| HBsAg (−) | | | | |
| Acute hepatitis-A | 7 | 0.012 ± 0.002 | 0.009–0.015 | 0 |
| Acute hepatitis-C | 10 | 0.008 ± 0.003 | 0.005–0.016 | 0 |
| Chronic hepatitis-C | 30 | 0.008 ± 0.002 | 0.004–0.017 | 0 |
| Normal Controls | 26 | 0.007 ± 0.003 | 0.006–0.014 | 0 |

Serum samples taken during periods of elevated ALT values from patients with the indicated diagnosis were diluted 1/500 and analyzed for IgG anti-HBc$^w$ reactivity by direct EIA. Data are expressed as mean ± s.d. absorbance ($OD_{492}$) values.

EXAMPLE 5

KINETICS OF IgM ANTI-HBc, IgG ANTI-HBc AND ANTI-HBc$^w$ ANTIBODY PRODUCTION IN ACUTE AND CHRONIC HBV INFECTION

To examine the kinetics of anti-HBc antibody production, temporal serum samples from 14 AH-B and 21 CH-B (4 CPH and 17 CAH) patients taken during a period of 4–5 months around the time of peak ALT elevations were analyzed for IgM anti-HBc, IgG anti-HBc and IgG anti-HBc$^w$. FIG. 4 shows the kinetics of antibody production to the HBcAg in AH-B and CH-B patients. Sequential serum samples from 14 AH-B (A) and 21 CH-B (B) patients were analyzed for IgM anti-HBc (●-●), IgG anti-HBc (▲-▲), and IgG anti-HBc$^w$ (Δ-Δ) at the indicated time points relative to peak elevations in ALT values. All antibodies were measured by direct EIA. The results are expressed as mean ±s.d. P/N ratios. N=0.015±0.005 (IgM anti-HBc assay); N=0.011±0.004 (IgG anti-HBc assay); and N=0.011±0.005 (IgG anti-HBc$^w$ assay).

Figure 4A:
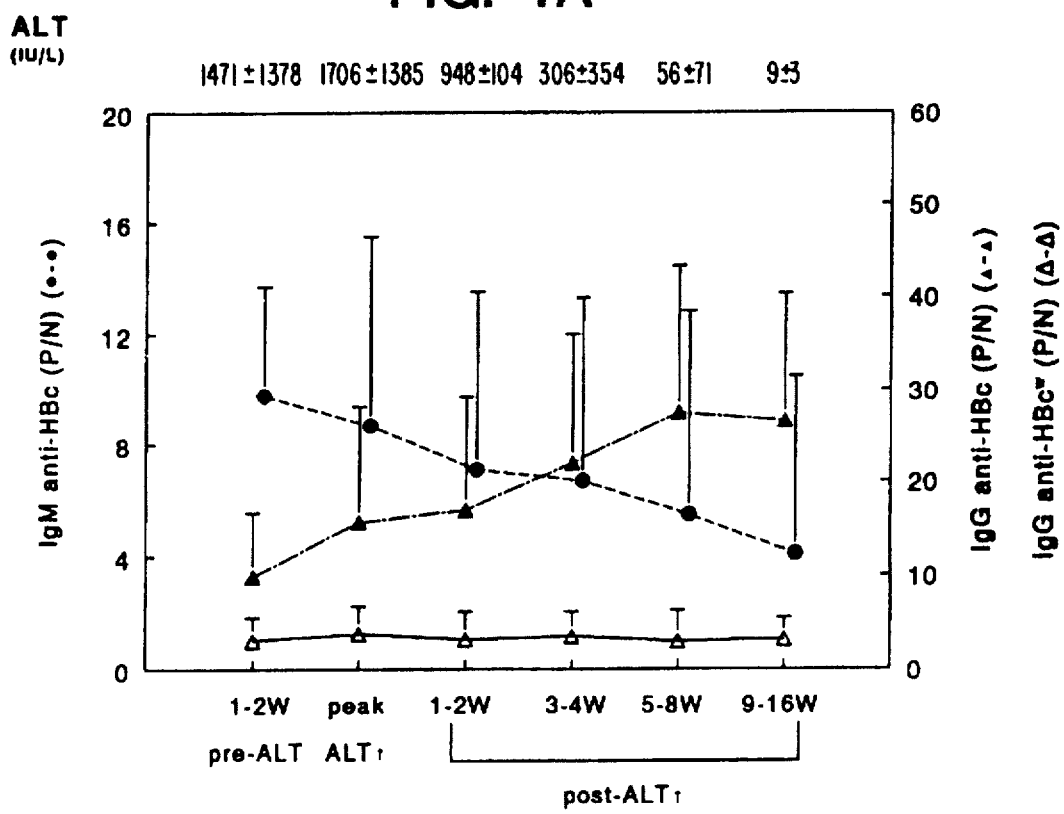
FIG. 4 is the kinetics of antibody production to the HBcAg in AH-B and CH-B patients. Sequential serum samples from AH-B (panel A) and CH-B (panel B) were analyzed for IgM anti-HBc (●-●), IgG anti-HBc (▲-▲), and IgG anti-HBc$^w$ (Δ-Δ).
Figure 4B:
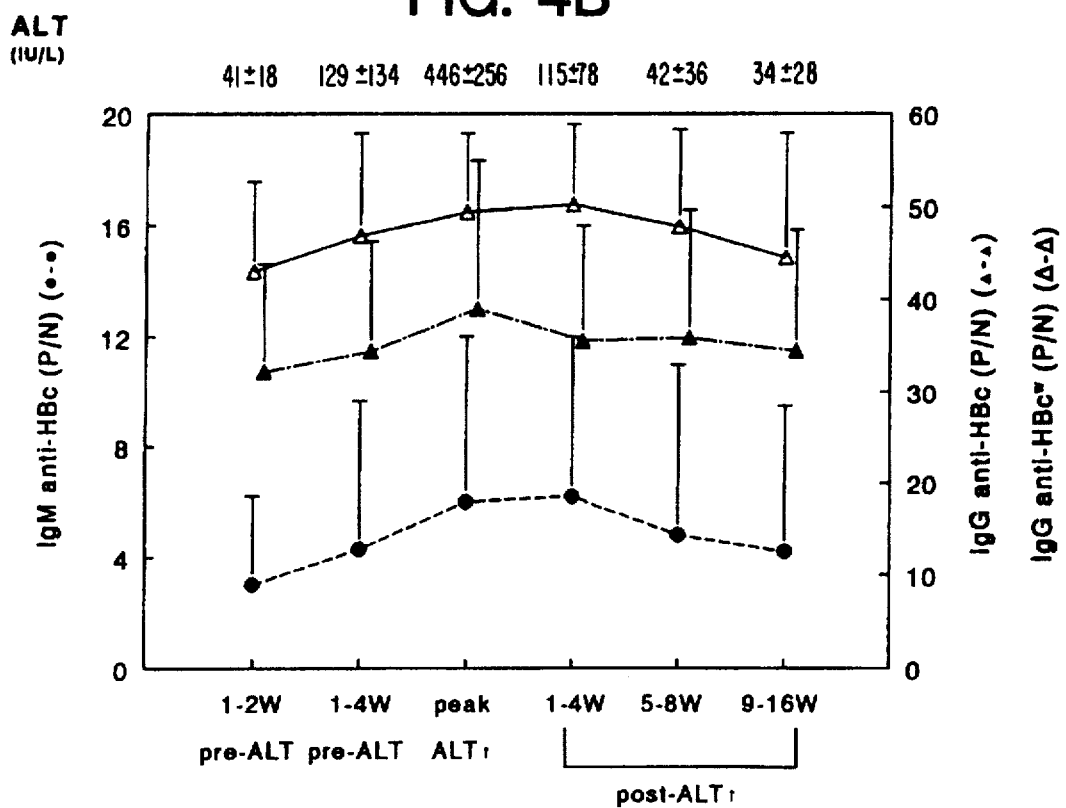

In AH-B patients, IgM anti-HBc levels were initially high before the peak ALT elevation and declined thereafter (from a mean of 9.8 to 4.1 P/N), conversely, the production of IgG anti-HBc was initially low and increased during resolution of the hepatitis (from a mean of 9 to 27.5 P/N), and IgG anti-HBc$^w$ production remained low to negative throughout the observation period (FIG. 4.A). In CH-B patients, the level of IgM anti-HBc was relatively low 5–8 weeks prior to liver injury, but increased in parallel with ALT elevation and declined thereafter (from a mean of 3.0 to 6.2 P/N) (FIG. 4B). The levels of IgG anti-HBc in CH-B patients remained quite high throughout the observation period (from a mean of 32.3 to 39.0 P/N), as did IgG anti-HBc$^w$ production (from a mean of 43.0 to 50.3 P/N) (FIG. 4.B). These data indicate that during the course of liver injury a single serum sample taken from an AH-B or CH-B patient may reflect fluctuating IgM and IgG anti-HBc antibody levels that may not clearly distinguish between an acute infection and an acute exacerbation of a chronic infection. In contrast, the anti-HBc$^w$ levels remain consistently low in AH-B patients and consistently high in CH-B patients before, during and after periods of liver injury (FIG. 4A, B).

Figure 5:
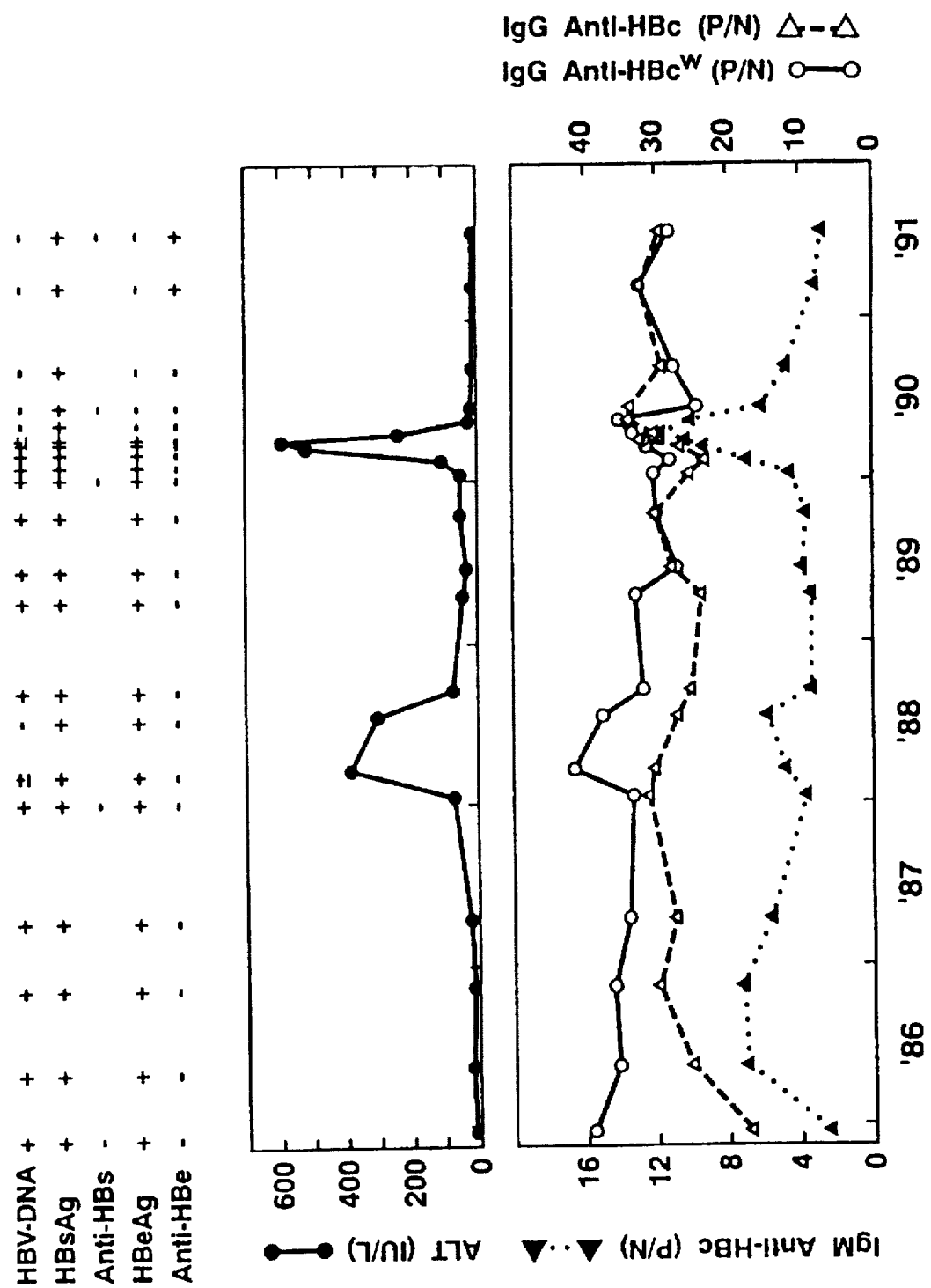
FIG. 5 is the serologic profile of a CH-B patient. The top panel shows standard serologic parameters.

The consistency and usefulness of the anti-HBc$^w$ assay is demonstrated in the serological profile of a single CH-B patient shown in FIG. 5. A CAH patient (H.M. a 22 year-old female) was monitored for a 6 year period during which two A.E. of liver injury (4/88 and 4/90) were recorded. The standard serologic parameters shown (top) were measured by commercial assays. IgM anti-HBc, IgG-anti-HBc, and IgG anti-HBc$^w$ were measured by direct EIA as described. The data are expressed as P/N ratios for each time point (▲-▲=IgM Anti-HBc; ●-●=ALT; Δ-Δ=IgG anti-HBc; ○-○=IgM anti-HBc$^w$).

This CH-B patient experienced two A.E. of liver injury in April of 1988 and in April of 1990. If this patient appeared in the clinic for the first time in April of 1990 without a prior history of HBV infection, the only serological marker that would indicate an A.E. of a chronic HBV infection rather than an acute HBV infection is the elevated anti-HBc$^w$ value. Note that the IgM anti-HBc value is significantly elevated during the period of maximum liver injury when the patient is most likely to seek medical attention.

EXAMPLE 6

IMMUNOLOGICAL CHARACTERIZATION OF THE HBc$^w$ EPITOPE

Figure 6A:
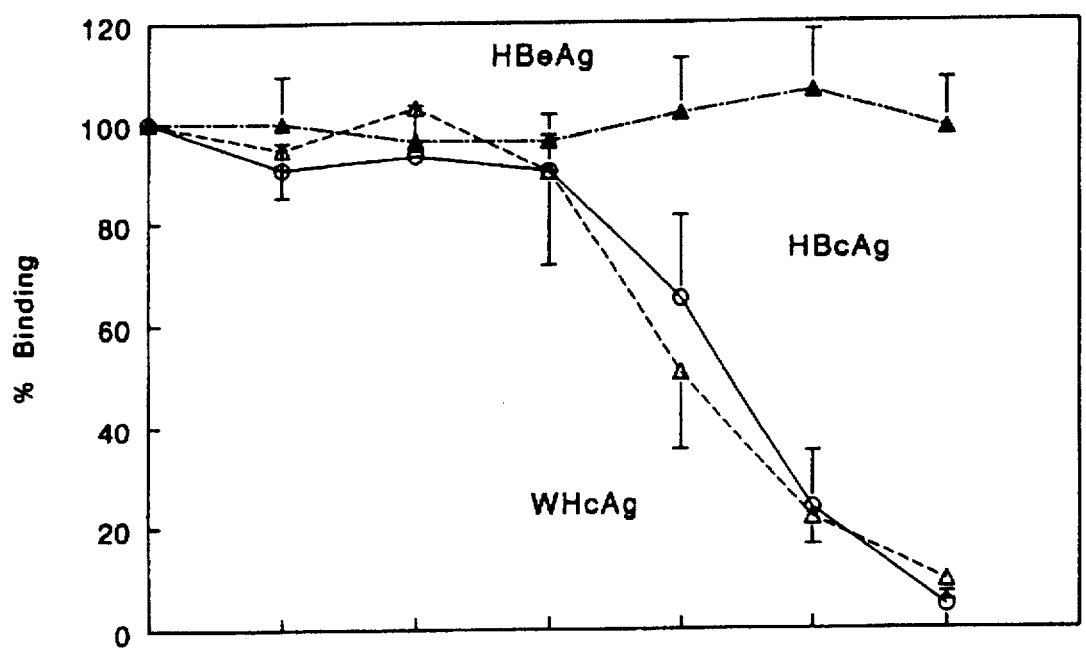
FIG. 6 is antigen inhibition analysis of CH-B patient sera. Panel A is anti-HBc$^w$ and panel B is anti-HBc assayed by direct EIA. (HBeAg, ▲-▲; HBcAg, ○-○; and WHcAg, Δ-Δ).
Figure 6B:
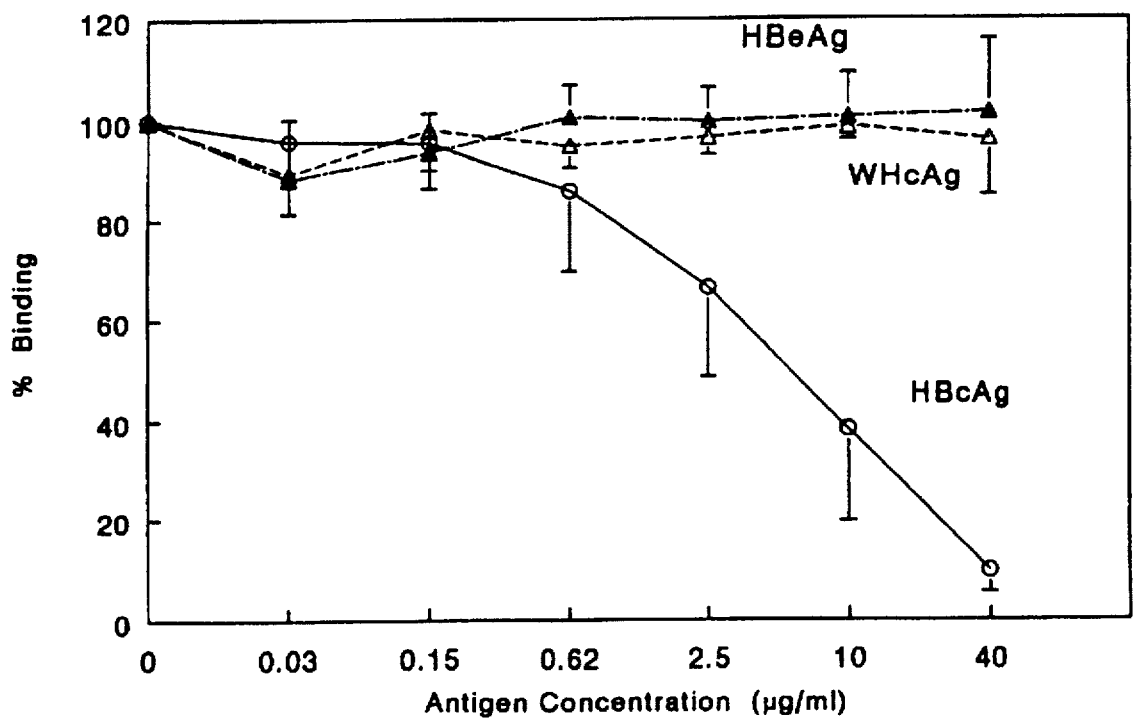

Although the production of IgG antibody reactive with WHcAg correlated with IgG anti-HBc antibody production in chronic HBV infection, it was necessary to confirm the antigenic relationship between the WHcAg and the HBcAg directly. For that purpose, a pool of sera obtained from 6 CH-B patients positive for anti-HBc$^w$ was analyzed in an antigen competition assay. FIG. 6 shows an antigen inhibition analysis of CH-B patient sera. Sera from 6 CH-B patients positive for anti-HBc and anti-HBc$^w$ antibodies were preincubated with the indicated concentrations of the soluble inhibitors HBcAg, WHcAg, or HBeAg overnight at 4° C. The residual anti-HBc$^w$ (A) or anti-HBc (B) reactivity was then assayed by direct EIA using solid-phase WHcAg or HBcAg, respectively, as solid-phase ligands. The data are expressed as percent binding compared to the absorbance value ($OD_{492}$) obtained without soluble inhibitor.

The CH-B patient sera was preincubated with soluble HBcAg, HBeAg or WHcAg prior to addition to either solid-phase WHcAg (FIG. 6A) or HBcAg (FIG. 6.B), and the percent of IgG binding to the solid-phase ligands as compared to unabsorbed CH-B patient sera was determined. The binding of CH-B patient IgG to solid-phase WHcAg was quantitatively inhibited by WHcAg and HBcAg to the same degree but was not inhibited by HBeAg (FIG. 6.A). This result indicates that the HBc$^w$ epitope(s) recognized by CH-B patient IgG is present on both the HBcAg and the WHcAg but not on the HBeAg.

In the reciprocal assay, the binding of CH-B patient IgG to solid-phase HBcAg was quantitatively inhibited only by HBcAg and not by WHcAg or HBeAg (FIG. 6.B). The inability of soluble WHcAg to inhibit the binding of CH-B patient IgG to HBcAg indicates that the HBc$^w$ epitope(s) is crossreactive with only a minor proportion of HBcAg epitopes, and that the HBc$^w$-specific antibody detected in CH-B patient sera represents only a minor component of the total IgG anti-HBc response. This is consistent with the observation that no HBcAg-specific Mab recognized the WHcAg (Table 2).

TABLE 2

THE HBc$^w$ EPITOPE IS NOT RECOGNIZED BY THE KNOWN HBcAG AND HBeAG SPECIFIC MONOCLONAL ANTIBODIES

| Antibody | | WHcAG | HBcAG | HBeAg |
|---|---|---|---|---|
| Mab Anti-HBc | 3105 | 0.01 | 1.29 | 0.16 |
| | 3120 | 0.04 | 1.99 | 0.08 |
| | 440 | 0.03 | 1.65 | 0.35 |
| | 442 | 0.01 | 0.58 | 0.11 |
| Mab Anti-HBe | 904 | 0.01 | 0.08 | 0.92 |
| | 905 | 0.02 | 0.10 | 1.39 |
| | 420 | 0.01 | 0.12 | 1.93 |
| | 422 | 0.01 | 0.09 | 1.53 |
| | 426 | 0.01 | 0.03 | 1.43 |
| Mab Anti-HBe peptide (2221) | | 0.69 | 0.63 | 2.00 |
| Poly Anti-HBc/e | | 0.12 | 2.0 | 2.00 |
| Poly Anti-WHc | | 1.90 | 0.16 | 0.11 |

Recombinant WHcAg, HBcAg and HBeAg were coated on the solid-phase (50 ng/well), and the panel of indicated antibodies were assayed for binding in direct EIA. Mabs were assayed at 0.5 µg/ml and polyclonal sera was diluted 1/8000. The data are expressed as absorbance ($OD_{492}$) values.

Similarly, a panel of HBeAg-specific Mabs also failed to recognize the WHcAg. Only Mab 2221 specific for residues 129–140 of the HBc/HBe antigens bound WHcAg (Table 2). The 129–140 sequence is highly conserved between WHcAg and HBcAg.

Figure 7:
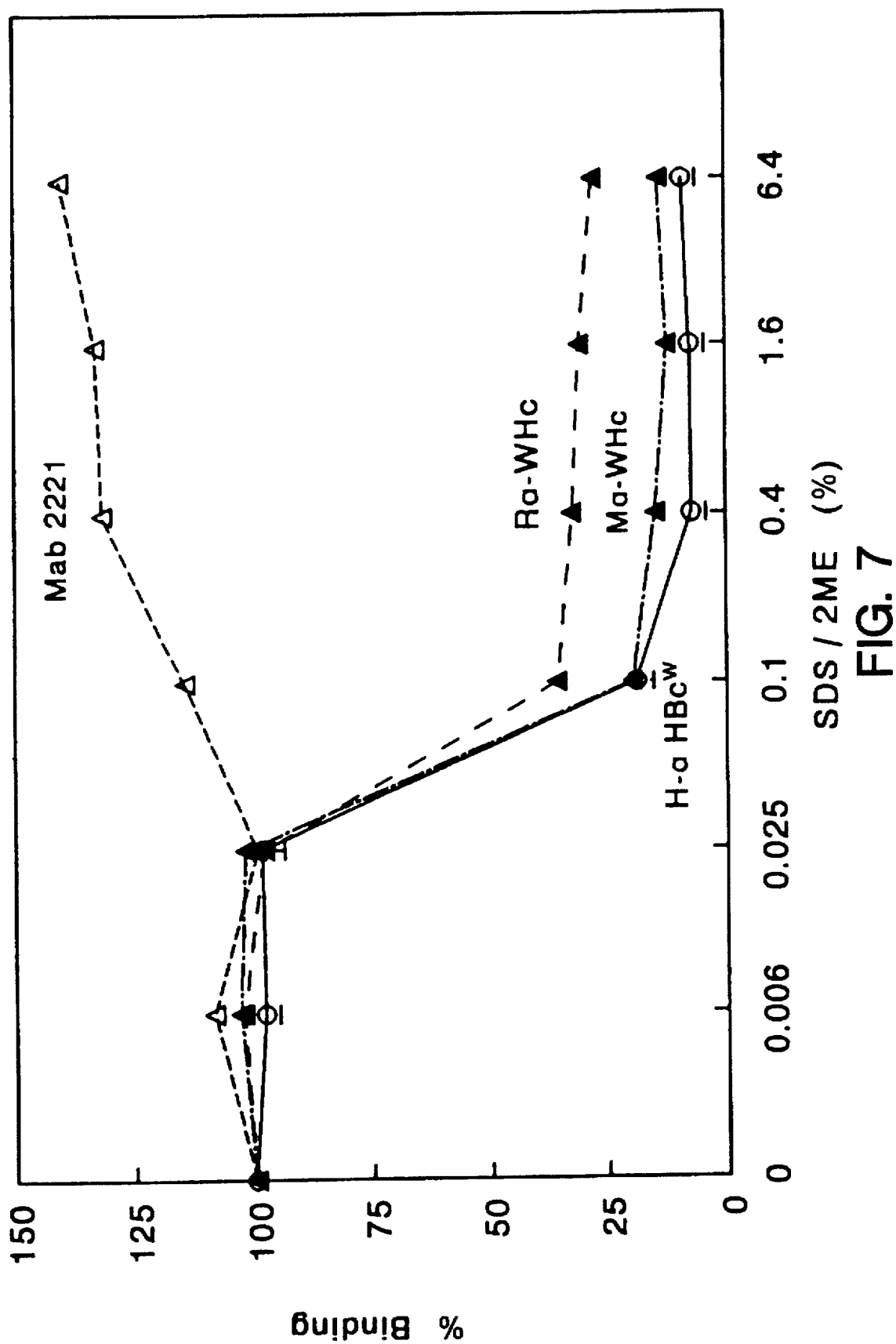
FIG. 7 shows the sensitivity of anti-HBc$^w$ reactivity to denaturation of woodchuck HcAg. (Mab 2221, Δ-Δ; Ra-WHC, ▲- - -▲; Ma-WHC, ▲-.-.- ▲; Ha-HBc$^w$, ○-○).

Next, the requirement for native WHcAg structure for binding by human anti-HBc$^w$ antibody was examined. Recombinant WHcAg was treated with a range of concentrations of SDS/2ME (0.006–6.4%), and human anti-HBc$^w$ IgG, derived from a group of CH-B patient sera, and mouse anti-WHc and rabbit anti-WHc IgG, produced by immunization with rWHcAg, were analyzed for binding to solid-phase denatured WHcAg. FIG. 7 shows sensitivity of anti-HBc$^w$ reactivity to denaturation of WHcAg. Recombinant WHcAg (1 mg/ml) was treated with the indicated concentrations of SDS/2ME for 2 hours at 37° C., and WHcAg (diluted 1000 X) was coated on the solid-phase (50 ng/well). Polyclonal mouse anti-WHc (Ma-WHc, ▲- - - ▲) polyclonal rabbit anti-WHc (Ra-WHc) (▲- - - ▲), monoclonal anti-HBe peptide (Mab 2221) (Δ-Δ), or human anti-HBc$^w$-positive antisera from 4 CH-B patients (Ha-HBc$^w$) (○-○) were added to the wells, and bound antibodies were detected by peroxidase-labeled anti-murine, rabbit or human Ig. The data are expressed as percent binding compared to the absorbance value ($OD_{492}$) obtained without SDS/2ME treatment.

The Mab 2221, which binds the linear peptidic epitope 129–140, served as a positive control to insure that adequate denatured WHcAg adhered to the solid-phase well. Binding of human anti-HBc$^w$ to WHcAg was very sensitive to denaturation of WHcAg, and was reduced 80% by the treatment of WHcAg with 0.1% SDS/2ME. Similarly, the binding of polyclonal murine and rabbit antisera raised against native WHcAg were equally sensitive to the denaturation of WHcAg. The conformational-dependence of human anti-HBc$^w$ was further demonstrated by the failure to detect binding of human anti-HBc$^w$ to a panel of WHcAg-derived overlapping peptides.

Lastly, to determine if the epitope(s) on WHcAg recognized by human anti-HBc$^w$ IgG was species-specific, antibody competition assays were performed between human anti-HBc$^w$ antisera and murine and rabbit polyclonal antibody raised against rWHcAg (Table 3). The binding to WHcAg of a panel of 4 CH-B patient sera, positive for anti-HBc$^w$ reactivity, was quantitatively inhibited by competitor rabbit and murine polyclonal anti-WHc antisera. Reciprocally, the binding to WHcAg of both rabbit and murine anti-WHc antisera were inhibited by a panel of 6 human anti-HBc$^w$-positive antisera used as competitors (Table 3). Therefore, the WHcAg crossreactive epitope(s) recognized by human anti-HBc$^w$-positive antisera is also recognized by mice and rabbits immunized with WHcAg.

TABLE 3

ANTI-HBc$^w$ ANTIBODY PRODUCTION IS NOT SPECIES SPECIFIC

| Primary Antibody | Competitor Antibody | Inhibition (%) | | |
|---|---|---|---|---|
| | | 1:100 | 1:500 | 1:2500 |
| H anti-HBc$^w$ (N = 4) | R anti-WHc | 96.7 ± 0.9 | 96.0 ± 0.8 | 91.7 ± 2.7 |
| | M anti-WHc | 91.2 ± 1.8 | 87.2 ± 5.3 | 77.2 ± 8.5 |
| R anti-WHc | H anti-HBc$^w$ (N = 6) | 40.7 ± 11.6 | 23.2 ± 17.0 | 17.2 ± 14.4 |
| M anti-WHc | H anti-HBc$^w$ (N = 6) | 36.2 ± 10.1 | 23.2 ± 12.0 | 14.5 ± 8.8 |

The indicated competitor antibodies polyclonal rabbit (R) or murine (M) anti-WHc, or human (H) anti-HBc$^w$ derived from CH-B patient sera were preincubated with solid-phase WHcAg (50 ng/well) for 2 hours at 37° C. Thereafter, the indicated primary antibodies were added to the wells and the percent inhibition by the competitor antibodies as compared to inhibition with preimmunization sera or normal human sera was determined.

The invention now being fully described, it will be apparent to one of ordinary skill in the art that various changes and modifications can be made without department from the spirit or scope of the invention.

We claim:

1. A method of diagnosing chronic hepatitis B virus (HBV) infection in a subject comprising:

(a) contacting a sample from a subject suspected of having chronic HBV infection with woodchuck hepatitis B virus core antigen; and (b) detecting the presence in said sample of antibody that binds woodchuck hepatitis B core antigen, wherein the presence of said antibody bound to said woodchuck hepatitis B core antigen indicates chronic hepatitis B virus infection in said subject.

2. The method of claim 1, wherein the sample is serum.

3. The method of claim 1, wherein the woodchuck hepatitis B core antigen is bound to a solid support.

4. The method of claim 1, wherein the detection includes the addition of second antibody that binds to the anti-woodchuck hepatitis B core antigen antibody.

5. The method of claim 4, wherein the second antibody is detectably labeled.

6. The method of claim 5, wherein the label is selected from the group consisting of enzymes, radioisotopes, fluorescent compounds, colloidal metals, chemiluminescent compounds, phosphorescent compounds, and bioluminescent compounds.

7. The method of claim 1, wherein the anti-woodchuck hepatitis B core antigen antibody detected in step (b) is isotype IgG.

8. The method of claim 7, further comprising detecting the level of IgM anti-hepatitis B core antigen antibody in the sample.

9. The method of claim 8, wherein the ratio of IgM anti-hepatitis B core antigen antibody to IgG anti-woodchuck hepatitis B core antigen antibody is determined.

10. The method of claim 1, wherein the chronic hepatitis is chronic active hepatitis or chronic persistent hepatitis.

11. The method of claim 1, wherein the chronic hepatitis is chronic persistant hepatitis.

* * * * *